United States Patent [19]

Kimura et al.

[11] 4,379,086

[45] Apr. 5, 1983

[54] METHOD OF PREPARING IMMUNOGLOBULIN SUITABLE FOR INTRAVENOUS ADMINISTRATION USING PEG

[75] Inventors: Tokusuke Kimura, Tokyo; Fumio Kurosu, Hasuda, both of Japan

[73] Assignee: Fujizoki Pharmaceutical Co., Ltd., Tokyo, Japan

[21] Appl. No.: 383,050

[22] Filed: May 28, 1982

[30] Foreign Application Priority Data

Jun. 9, 1981 [JP] Japan .................................. 56/87503

[51] Int. Cl.³ ................................................ C07G 7/00
[52] U.S. Cl. .................................. 260/112 B; 424/101
[58] Field of Search ...................... 260/112 B; 424/101

[56] References Cited

U.S. PATENT DOCUMENTS 3,415,804 12/1968 Polson ............................ 260/112 B
3,763,135 10/1973 Shanbrom et al. ............... 260/112 B
3,808,189 4/1974 Breuer ............................. 260/112 B
4,093,606 6/1978 Coval .............................. 260/112 B
4,124,576 11/1978 Coval .............................. 260/112 B
4,296,027 10/1981 Condie ............................ 260/112 B

FOREIGN PATENT DOCUMENTS 1372953 11/1974 United Kingdom .

OTHER PUBLICATIONS

J. Am. Chem. Soc. 71, 541–550 (1949), Cohn.

Primary Examiner—Howard E. Schain
Attorney, Agent, or Firm—Flynn, Thiel, Boutell & Tanis

[57] ABSTRACT

The method of preparing immunoglobulin (IgG) suitable for intravenous administration comprising the fractionation of Cohn Plasma Fraction II with polyethylene glycol having a molecular weight of 4000 at predetermined concentrations and under selected pH conditions.

1 Claim, No Drawings

METHOD OF PREPARING IMMUNOGLOBULIN SUITABLE FOR INTRAVENOUS ADMINISTRATION USING PEG

BACKGROUND OF THE INVENTION

The present invention relates to a method of preparing immunoglobulin (IgG) suitable for intravenous administration. More particularly, the present invention relates to a method of preparing immunoglobulin not containing aggregates of immunoglobulin.

In the present invention, immunoglobulin in powder form, which is referred to as Cohn Plasma Fraction II, is employed as a starting material. Said Cohn Plasma Fraction II (hereinafter is referred to as Cohn Fraction II in short) is obtained by the so-called Cohn Method 9 described in J. Am. Chem. Soc. 71, 541-550 (1949).

Immunoglobulin (IgG) is widely used as a therapeutic agent, and generally, immunoglobulin is administrated by intravenous injection. However, certain impurities such as aggregates of immunoglobulin occasionally contained in immunoglobulin products render the administration of such immunoglobulin by intravenous injection hazardous.

Various methods for the production or the purification of immunoglobulin have been disclosed in the literatures, for instance, U.S. Pat. Nos. 3,415,804, 3,763,135 and 4,093,606, and British Pat. No. 1,372,953.

It is an object of this invention to provide a method of preparing immunoglobulin (IgG) in high purity and suitable for intravenous administration from Cohn Fraction II under conditions different from those disclosed in the specifications of the patents mentioned above.

SUMMARY OF THE INVENTION

The present invention will be illustrated in the following:

Immunoglobulin in powder form (Cohn Fraction II) is dissolved in a buffer solution having a pH of 7 to 8 such as 0.033 M phosphate buffer solution (pH: 7.5 to 7.7) to obtain a solution containing immunoglobulin in a concentration of 2 to 3%. To this solution is added polyethylene glycol (PEG) having a molecular weight of 4000 so as to obtain a solution containing PEG in a concentration of 3 to 4%. The solution is centrifuged to result in a precipitate (aggregates of immunoglobulin) which is discarded and a supernatant. To the supernatant which has been obtained by removing the precipitate (aggregates of immunoglobulin) is added PEG (M.W. 4000) at a pH of 6.5 to 7.0 to obtain a solution containing PEG in a concentration of 6 to 8%. The solution is centrifuged to obtain purified immunoglobulin in a paste form. The paste of immunoglobulin is dissolved in a solution containing glucose and sodium chloride in concentrations of 2.25% and 0.85% respectively. The solution is subjected to filtration of bacteria to obtain a filtrate. The filtrate is freeze-dried to obtain purified immunoglobulin in powder form.

0.033 M phosphate buffer solution having a pH of from 7 to 8 can be prepared by mixing 1 part by volume of 0.033 M aqueous solution of $NaH_2PO_4$ with from 5 to 8 parts by volume of 0.033 M aqueous solution of $Na_2HPO_4$.

EXAMPLE 600 g of crude immunoglobulin (Cohn Fraction II) was dissolved in a 0.033 M phosphate buffer solution (pH 7.7) to obtain a solution containing immunoglobulin in a concentration of 3%. To the solution was added 147 ml of a 50% aqueous solution of polyethylene glycol (PEG M.W. 4000) to obtain a solution containing PEG in a concentration of 4%. Aggregates of immunoglobulin produced as a precipitate was removed by centrifugation. The supernatant thus obtained was filtered, and to the filtrate was added 157 ml of a 50% aqueous solution of PEG to obtain a solution containing PEG in a concentration of 8%. The solution was centrifuged to obtain purified immunoglobulin in a paste form. The paste of immunoglobulin was dissolved in an aqueous solution containing glucose and sodium chloride in concentrations of 2.25% and 0.85% respectively. The solution was subjected to filtration of bacteria to obtain a filtrate. The filtrate was freeze-dried to obtain immunoglobulin for use in intravenous administration.

Immunoglobulin thus obtained has a value of anti-complementary activity (ACA value) less than 10 unit/ml, and therefore, it can be used for intravenous administration.

We claim:

1. The method of preparing immunoglobulin suitable for intravenous administration which comprises the steps of:
   (1) dissolving Cohn Plasma Fraction II in a Phosphate buffer solution having a pH of 7.0 to 8.0 to a concentration of 2% to 3%,
   (2) adding polyethylene glycol (PEG) having a molecular weight of 4000 to the solution to a concentration of 3% to 4%,
   (3) removing aggregates of immunoglobulin produced and precipitated by centrifugation,
   (4) adding PEG (M.W. 4000) to the supernatant to a concentration of 6% to 8% at a pH of 6.5 to 7.0, and
   (5) separating immunoglobulin as a paste from the aqueous liquid.

* * * * *